(12) United States Patent
Wang et al.

(10) Patent No.: US 12,245,993 B2
(45) Date of Patent: Mar. 11, 2025

(54) VITAMIN K2 MICROCAPSULE, PREPARATION METHOD THEREOF AND USE THEREOF IN MANUFACTURE OF MEDICAMENT FOR PREVENTING OR TREATING CARDIOVASCULAR AND CEREBROVASCULAR DISEASES

(71) Applicants: Xiamen Kingdomway Biotech. Co., Ltd., Fujian (CN); Xiamen Kingdomway Group Company, Fujian (CN)

(72) Inventors: Xuerui Wang, Fujian (CN); Jinhong Liu, Fujian (CN); Wenji Wang, Fujian (CN); Murong Lin, Fujian (CN); Chuquan Wei, Fujian (CN)

(73) Assignees: Xiamen Kingdomway Biotech. Co., Ltd., Fujian (CN); Xiamen Kingdomway Group Company, Fujian (CN)

( * ) Notice: Subject to any disclaimer, the term of this patent is extended or adjusted under 35 U.S.C. 154(b) by 813 days.

(21) Appl. No.: 17/442,784

(22) PCT Filed: Sep. 28, 2020

(86) PCT No.: PCT/CN2020/118330
§ 371 (c)(1),
(2) Date: Sep. 24, 2021

(87) PCT Pub. No.: WO2022/061870
PCT Pub. Date: Mar. 31, 2022

(65) Prior Publication Data
US 2022/0304948 A1    Sep. 29, 2022

(51) Int. Cl.
| A61K 31/122 | (2006.01) |
| A61K 9/48 | (2006.01) |
| A61K 9/50 | (2006.01) |

(52) U.S. Cl.
CPC .......... *A61K 31/122* (2013.01); *A61K 9/4858* (2013.01); *A61K 9/4875* (2013.01); *A61K 9/5036* (2013.01); *A61K 9/5089* (2013.01)

(58) Field of Classification Search
CPC .................... A23V 2002/00; A23V 2250/7144
See application file for complete search history.

(56) References Cited

U.S. PATENT DOCUMENTS 11,090,276 B2    8/2021    Aukrust et al.

FOREIGN PATENT DOCUMENTS

| CN | 101422446 A | 5/2009 |
| CN | 101534807 A | 9/2009 |
| CN | 106074377 A | 11/2016 |
| CN | 106455667 A | 2/2017 |
| CN | 110693848 A | 1/2020 |
| WO | 2016044805 A1 | 3/2016 |

OTHER PUBLICATIONS

Cn106455667, Reidun et al, Machine Translation, pp. 1-22. (Year: 2017).*
Cn110693848, Xiang et al, Machine Translation, pp. 1-12. (Year: 2019).*
CN 101422446 A, May 6, 2009, Machine-Assisted English Translation.
CN 101534807 A, Sep. 16. 2009, Machine-Assisted English Translation.
CN 106074337 A, Nov. 9, 2016, Machine-Assisted English Translation.
CN 106455667 A, Feb. 22, 2017, U.S. Pat. No. 11,090,276 B2.
CN 110693848 A, Jan. 17, 2020, Machine-Assisted English Translation.
Zhaofei, Dr. Chen, "Nutrition, Immunity, Longevity", China Society Press, pp. 136-138, Sep. 2016, English Translation of Relevant Portions provided by CCPIT Patent and Trademark Office on Oct. 7, 2021.
International Search Report for Application No. PCT/CN2020/118330 dated May 26, 2021, 5 pages.
English language abstract and machine-assisted English translation for CN 101422446 A extracted from espacenet.com database on Oct. 4, 2021, 6 pages.
English language abstract and machine-assisted English translation for CN 101534807 A extracted from espacenet.com database on Oct. 4, 2021, 27 pages.
English language abstract and machine-assisted English translation for CN 106074377 A extracted from espacenet.com database on Oct. 4, 2021, 27 pages.
English language abstract for CN 1064556677 A extracted from espacenet.com database on Oct. 4, 2021, 2 pages.

(Continued)

*Primary Examiner* — Trevor Love
(74) *Attorney, Agent, or Firm* — Howard & Howard Attorneys PLLC

(57) ABSTRACT

The present disclosure pertains to the technical field of vitamin K2, and relates to a vitamin K2 microcapsule, a preparation method thereof, and use thereof in the manufacture of a medicament for preventing and treating cardiovascular and cerebrovascular diseases. The vitamin K2 microcapsule contains the following components by weight: 0.001 to 10 parts of vitamin K2, 5 to 30 parts of polyunsaturated fatty acid source, 0.1 to 10 parts of vitamin E-polyethylene glycol succinate, 50 to 95 parts of water-phase wall material and 0.01 to 10 parts of antioxidant, the polyunsaturated fatty acid source contains an ω-6 source and an ω-3 source, and the antioxidant is a water-phase antioxidant and/or an oil-phase antioxidant. The vitamin K2 microcapsule prepared by the method of the present disclosure has good water solubility, good stability and high bioavailability, can significantly improve the preventive and/or therapeutic effects on cardiovascular and cerebrovascular diseases, and has broad application prospects.

15 Claims, No Drawings

(56) References Cited

OTHER PUBLICATIONS

English language abstract and machine-assisted English translation for CN 110693848 A extracted from espacenet.com database on Oct. 4, 2021, 10 pages.

English translation of relevant portions of Zhaofei, Dr. Chen, "Nutrition, Immunity, Longevity", China Society Press, 2016, pp. 136-138 provided by CCPIT Patent and Trademark Law Office on Oct. 7, 2021, 5 pages; and Chinese language document of Zhaofei, Dr. Chen, "Nutrition, Immunity, Longevity", China Society Press, 2016, pp. 136-138.

* cited by examiner

VITAMIN K2 MICROCAPSULE, PREPARATION METHOD THEREOF AND USE THEREOF IN MANUFACTURE OF MEDICAMENT FOR PREVENTING OR TREATING CARDIOVASCULAR AND CEREBROVASCULAR DISEASES

CROSS-REFERENCE TO RELATED APPLICATIONS

The present application is the National Stage of International Patent Application No. PCT/CN2020/118330 filed on Sep. 28, 2020, which is hereby expressly incorporated herein by reference in its entirety.

TECHNICAL FIELD

The present disclosure pertains to the technical field of vitamin K2, and specifically relates to a vitamin K2 microcapsule, a preparation method thereof, and use thereof in manufacture of a medicament for preventing or treating cardiovascular and cerebrovascular diseases.

BACKGROUND ART

Cardiovascular and cerebrovascular diseases are the manifestation of systemic vascular diseases or systemic vascular diseases in the heart and brain, and generally refer to ischemic or hemorrhagic diseases of heart, brain and whole body tissues caused by hyperlipidemia, high blood viscosity, atherosclerosis, hypertension and so on. With the improvement of human living standard, the change of dietary structure and the aging of the population, the incidence of cardiovascular and cerebrovascular diseases is increasing year by year. Cardiovascular and cerebrovascular diseases are serious threats to human health, and characterized by high prevalence, high morbidity and high mortality, especially for middle-aged and elderly people over 50. At present, the main method for handling cardiovascular and cerebrovascular diseases is prevention, and the main means thereof are to control risk factors and antithrombosis. Therefore, it has become an arduous and urgent task for medical workers to develop safe and effective drugs and related preparations for the prevention and/or treatment of cardiovascular and cerebrovascular diseases.

Vitamin K2, also known as Menaquinone, is usually represented by MK. It is composed of a group of compounds, a total of 14 forms, the difference lies in the length of the side chain, the representative molecules are MK-4 and MK-7. Among them, MK-7 is characterized by wide range of functions, high safety, strong activity, long half-life, etc., and plays a very important role in the growth and metabolism of cells and the prevention or treatment of calcification in heart and cerebral vessels and renal vessels. Vitamin K2 promotes bone and heart health by activating two proteins that balance calcium in the body. The Office of Dietary Supplements of the National Institutes of Health evaluated vitamin K2 (MK-7) as a revolutionary and multipotent vitamin, which has broad application prospects for health care. Relevant studies have found that patients with novel coronavirus COVID-19 in deteriorated state are lack of sufficient vitamin K2; especially, in the context of the global epidemic, the public has a new interest in vitamin K2 and its potential role in immune, health and COVID-19 outcomes. However, the content of vitamin K2 (MK-7) in natural foods is extremely low, and it is basically impossible to get enough vitamin K2 (MK-7) through food to meet the body's various needs.

Vitamin K2 is a fat-soluble drug with very low solubility in water. Therefore, it is difficult to digest and absorb in the gastrointestinal tract after oral administration, and its bioavailability is extremely low. In addition, vitamin K2 is quite sensitive to light and oxygen, and is easily decomposed when exposed to light. In view of this, even though vitamin K2 has good health pharmacological effects, if its solubility in aqueous medium and its stability are not improved, it is still difficult to achieve the desired value in clinical efficacy. In addition, vitamin K2 is mainly extracted from natto or produced by microbial fermentation, which is difficult to artificially synthesize. Therefore, there is an urgent need to develop a vitamin K2 product with higher water solubility, stability and bioavailability, which can not only ensure that vitamin K2 reaches the required concentration of health pharmacological effects in the body, but also save raw materials and reduce production costs.

SUMMARY OF THE DISCLOSURE

The purpose of the present disclosure is to overcome the shortcomings of poor water solubility and stability and low bioavailability of vitamin K2, to provide a vitamin K2 microcapsule capable of improving the water solubility, stability and bioavailability of vitamin K2, as well as a method for preparing the same, and use thereof for the manufacture of a medicament for preventing or treating cardiovascular and cerebrovascular diseases.

The inventors of the present disclosure have found through continuous experiments that vitamin K2, ω-6 source/ω-3 source, vitamin E-polyethylene glycol succinate, water-phase wall material and antioxidants in weight ratio of (0.001-10):(5-30):(0.1-10):(50-95):(0.01-10) are used as raw materials to make vitamin K2 microcapsules. On the one hand, vitamin K2, ω-6 and ω-3 have a synergistic effect in the prevention and/or treatment of cardiovascular and cerebrovascular diseases, ω-6 and ω-3 can significantly improve the bioavailability of vitamin K2; on the other hand, making vitamin K2 into microcapsules can effectively solve the problem of poor water solubility and improve its stability, the microcapsules can effectively encapsulate vitamin K2 in the core material, isolate the light and prevent vitamin K2 from contacting the air, prevent its migration and oxidation, so as to improve the stability of vitamin K2 in the microcapsules. In addition, in the preparation process of vitamin K2 microcapsules, vitamin E-polyethylene glycol succinate (TPGS) is divided into two portions in certain proportion and added to the oil phase and the water phase respectively, which can greatly reduce the homogenization pressure of emulsification, improve the stability of vitamin K2. This dual effect of internally relying on vitamin E-polyethylene glycol succinate and externally relying on microcapsule packaging can significantly improve the water solubility and stability of vitamin K2, which is more conducive to its biological activity. Based on this, the present disclosure has been completed.

Specifically, the present disclosure provides a vitamin K2 microcapsule, wherein the vitamin K2 microcapsule comprises the following components in parts by weight: 0.001 to 10 parts of vitamin K2, 5 to 30 parts of polyunsaturated fatty acid source, 0.1 to 10 parts of vitamin E-polyethylene glycol succinate, 50 to 95 parts of water-phase wall material, and 0.01 to 10 parts of antioxidant, the polyunsaturated fatty acid source comprises ω-6 source and ω-3 source, and the antioxidant is water-phase antioxidant and/or oil-phase antioxidant.

Further, the vitamin K2 microcapsule comprises the following components in parts by weight: 0.005 to 5 parts of vitamin K2, 10 to 25 parts of polyunsaturated fatty acid source, 0.5 to 5 parts of vitamin E-polyethylene glycol succinate, 55 to 90 parts of water-phase wall material, and 0.05 to 5 parts of antioxidant.

Further, the vitamin K2 is in the MK-7 configuration.

Further, the mass ratio of ω-6 and ω-3 in the polyunsaturated fatty acid source is (0.5 to 4):1, in some embodiments, the ratio is (1 to 2):1, in some embodiments, the ratio is 1.5:1.

Further, the ω-3 source is at least one selected from the group consisting of DHA algae oil, fish oil, linseed oil, perilla seed oil, low erucic acid rapeseed oil, walnut oil, zanthoxylum seed oil and soybean oil.

Further, the ω-6 source is at least one selected from the group consisting of ARA oil, grape seed oil, safflower seed oil, soybean oil, low erucic acid rapeseed oil, walnut oil, sunflower oil and sesame oil.

Further, the water-phase wall material is at least one selected from the group consisting of protein compound wall material, carbohydrate wall material and modified starch.

Further, the protein compound wall material is at least one selected from the group consisting of sodium caseinate, soy protein, prolamin and whey protein.

Further, the carbohydrate wall material is at least one selected from the group consisting of Arabic gum, white granulated sugar, cyclodextrin, maltodextrin, solid corn syrup and dry glucose syrup powder.

Further, the modified starch is starch sodium octenyl succinate and/or starch sodium dodecenyl succinate.

Further, the water-phase antioxidant is at least one selected from the group consisting of sodium ascorbate, ascorbic acid and sodium citrate.

Further, the oil-phase antioxidant is at least one selected from the group consisting of lecithin, natural VE, rosemary extract and ascorbyl palmitate.

Further, the vitamin K2 microcapsule further comprises at least one of glidant, flavoring agent and coloring agent.

Further, the glidant, flavoring agent and coloring agent each independently have content of 0 to 5 parts by weight, in some embodiments, the glidant, flavoring agent and coloring agent each independently have content of 0 to 2 parts by weight.

The present disclosure also provides a method for preparing the vitamin K2 microcapsule, the method comprising:

(1) the water-phase wall material, part of vitamin E-polyethylene glycol succinate and optional water-phase antioxidant, glidant, flavoring agent and coloring agent are dispersed in water to obtain a water-phase material; vitamin K2, polyunsaturated fatty acid source, the remaining vitamin E-polyethylene glycol succinate and optional oil-phase antioxidant are mixed uniformly to obtain an oil-phase material; the water-phase material and the oil-phase material have a vitamin E-polyethylene glycol succinate weight ratio of (2 to 6):1;

(2) the water-phase material and the oil-phase material are mixed, emulsified under high-speed shearing, and homogenized under a pressure of 30 to 50 MPa to obtain an emulsion with an oil droplet particle size of ≤100 nanometer, and then the obtained emulsion is subjected to spray-drying to obtain a vitamin K2 microcapsule.

Further, in step (1), the water-phase wall material, part of vitamin E-polyethylene glycol succinate and optional water-phase antioxidant, glidant, flavoring agent and coloring agent are dispersed in water by a method that comprises: dissolving the water-phase wall material in 35° C. to 45° C. water, performing ultrasonic dispersion under an inert atmosphere to obtain a wall material aqueous solution, passing the solution through a ultrasonic probe in a countercurrent circulation mode, and then adding the part of vitamin E-polyethylene glycol succinate and optional water-phase antioxidant, glidant, flavoring agent and coloring agent into the wall material aqueous solution, and mixing uniformly under an inert atmosphere to obtain the water-phase material.

Further, in step (1), the ultrasonic dispersion is performed under a condition comprising an ultrasonic power of 240 to 480 W and an ultrasonic time of 10 to 30 min.

Further, in step (1), the vitamin K2, polyunsaturated fatty acid source, the remaining vitamin E-polyethylene glycol succinate and optional oil-phase antioxidant are mixed uniformly by a method that comprises: heating the vitamin K2, polyunsaturated fatty acid source, the remaining vitamin E-polyethylene glycol succinate and optional oil-phase antioxidant under an inert atmosphere to 35° C. to 50° C., keeping warm and stirring until these components are completely dissolved, thereby obtaining the oil-phase material.

Further, in step (2), the water-phase material and the oil-phase material are mixed by a method that comprises: simultaneously discharging and mixing the water-phase material and the oil-phase material at a mass ratio of (1.5 to 2.5):1.

Further, in step (2), the spray-drying is performed under a condition comprising a spray inlet air temperature of 140° C. to 170° C., an outlet air temperature of 80° C. of 95° C., an atomizer frequency of 165 to 200 Hz, and a cooling air temperature of 16° C. to 22° C., and a feed temperature of 50° C. to 60° C.

The present disclosure also provides a vitamin K2 microcapsule as prepared by the above method.

The present disclosure also provides use of the vitamin K2 microcapsule as a dietary supplement or a health food.

In addition, the present disclosure also provides use of the vitamin K2 microcapsule in the manufacture of a medicament for preventing or treating cardiovascular and cerebrovascular diseases.

The vitamin K2 microcapsule obtained by adopting the method provided by the present disclosure can significantly improve the water solubility, stability and bioavailability of vitamin K2, can significantly improve the preventive and/or therapeutic effects thereof on cardiovascular and cerebrovascular diseases, and have broad application prospects.

DETAILED DESCRIPTION OF EMBODIMENTS

In the vitamin K2 microcapsule, the vitamin K2 has a content of 0.001 to 10 parts by weight, specifically 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, 10 parts by weight, etc., in some embodiments, the vitamin K2 has a content of 0.005 to 5 parts by weight. The vitamin K2 can be any one of its 14 forms and any combination thereof, in some embodiments, the vitamin K2 is in the MK-7 configuration, because compared with other configurations, the MK-7 configuration is characterized by wide range of functions, high safety, strong activity and long half-life, and the vitamin K2 microcapsule obtained thereby is more effective in preventing and/or treating cardiovascular and cerebrovascular diseases.

In the vitamin K2 microcapsule, the polyunsaturated fatty acid source has a content of 5 to 30 parts by weight, specifically 5, 6, 7, 8, 9, 10, 11, 12, 13, 14, 15, 16, 17, 18, 19, 20, 21, 22, 23, 24, 25, 26, 27, 28, 29, 30 parts by weight, etc., in some embodiments, the polyunsaturated fatty acid source has a content of 10 to 25 parts by weight. The polyunsaturated fatty acid refers to a straight-chain fatty acid containing two or more double bonds and having a carbon chain length of 18 to 22 carbon atoms. According to the position of the first double bond carbon atom at the methyl end, the polyunsaturated fatty acids can be divided into ω-3 type and ω-6 type polyunsaturated fatty acids. Therein, the ω-3 type polyunsaturated fatty acids include α-linolenic acid (ALA), eicosapentaenoic acid (EPA) and docosahexaenoic acid (DHA). The ω-3 source may specifically be at least one selected from the group consisting of DHA algae oil, fish oil, linseed oil, perilla seed oil, low erucic acid rapeseed oil, walnut oil, zanthoxylum seed oil and soybean oil. The ω-6 type polyunsaturated fatty acids include linoleic acid (LA), γ-linolenic acid (GLA) and arachidonic acid (ARA). The ω-6 source may specifically be at least one selected from the group consisting of ARA oil, grape seed oil, safflower seed oil, soybean oil, low erucic acid rapeseed oil, walnut oil, sunflower oil and sesame oil. Since the ω-3 type polyunsaturated fatty acids and the ω-6 type polyunsaturated fatty acids require the same enzyme system in the metabolism process of the body, there is a certain competitive relationship between them. In order to be more suitable for absorption in the body, in some embodiments, the ω-6 and the ω-3 in the polyunsaturated fatty acid source have a mass ratio of (0.5 to 4):1, in some embodiments, the ratio is (1 to 2):1, in some embodiments, the ratio is 1.5:1.

The vitamin E-polyethylene glycol succinate (TPGS) is formed by esterification of vitamin E succinate and polyethylene glycol, including d-α-vitamin E-polyethylene glycol succinate (d-TPGS) and dl-α-vitamin E-polyethylene glycol succinate (dl-TPGS). The vitamin E-polyethylene glycol succinate has the advantages of PEG, that is, long circulation in the body, long half-life, and improved cellular uptake of drug, and has great advantages in the application of drug delivery systems. In addition, the vitamin E-polyethylene glycol succinate can inhibit the function of P-glycoprotein (P-g) to promote drug absorption, and has an antioxidant effect. In the vitamin K2 microcapsule, the vitamin E-polyethylene glycol succinate has a content of 0.1 to 10 parts by weight, specifically 0.1, 0.5, 1, 2, 3, 4, 5, 6, 7, 8, 9, 10 parts by weight, etc., in some embodiments, the vitamin E-polyethylene glycol succinate has a content of 0.5 to 5 parts by weight.

In the vitamin K2 microcapsule, the water-phase wall material has a content of 50 to 95 parts by weight, specifically 50, 55, 60, 65, 70, 75, 80, 85, 90, 95 parts by weight, etc., in some embodiments, the water-phase wall material has a content of 55 to 90 parts by weight. The water-phase wall material can be at least one selected from the group consisting of protein compound wall material, carbohydrate wall material and modified starch. Therein, specific examples of the protein compound wall material include, but are not limited to: at least one of sodium caseinate, soy protein, gliadin and whey protein. Specific examples of the carbohydrate wall material include, but are not limited to: at least one of Arabic gum, white granulated sugar, cyclodextrin, maltodextrin, solid corn syrup and dry glucose syrup powder. Specific examples of the modified starch include, but are not limited to: starch sodium octenyl succinate and/or starch sodium dodecenyl succinate.

In the vitamin K2 microcapsule, the antioxidant has a content of 0.01 to 10 parts by weight, specifically 0.01, 0.05, 0.1, 0.5, 1, 2, 3, 4, 5, 6, 7, 8, 9, 10 parts by weight, in some embodiments, the antioxidant has a content of 0.05 to 5 parts by weight. The antioxidant may be an oil-phase antioxidant, a water-phase antioxidant, or a combination of the two, and specific examples thereof include, but are not limited to: at least one of lecithin, natural VE, rosemary extract, ascorbic acid palmitate, sodium ascorbate, ascorbic acid, and sodium citrate.

The vitamin K2 microcapsule may further comprise at least one of glidant, flavoring agent and coloring agent. Therein, the glidant, flavoring agent and coloring agent may have a content of each independently 0 to 5 parts by weight, in some embodiments, the glidant, flavoring agent and coloring agent have a content of each independently 0 to 2 parts by weight. The types of the glidant, flavoring agent and coloring agent can all be conventionally selected in the art, and those skilled in the art know well about this, and thus it will not be repeated here.

The method for preparing the vitamin K2 microcapsule provided by the present disclosure comprises:

(1) the water-phase wall material, part of vitamin E-polyethylene glycol succinate and optional water-phase antioxidant, glidant, flavoring agent and coloring agent are dispersed in water to obtain a water-phase material; vitamin K2, polyunsaturated fatty acid source, the remaining vitamin E-polyethylene glycol succinate and optional oil-phase antioxidant are mixed uniformly to obtain an oil-phase material; the water-phase material and the oil-phase material have a vitamin E-polyethylene glycol succinate weight ratio of (2 to 6):1;

(2) the water-phase material and the oil-phase material are mixed, emulsified under high-speed shearing, and homogenized under a pressure of 30 to 50 MPa to obtain an emulsion with an oil droplet particle size of ≤100 nanometer, and then the obtained emulsion is subjected to spray-drying to obtain a vitamin K2 microcapsule.

The present disclosure does not specifically limit the method that the water-phase wall material, part of vitamin E-polyethylene glycol succinate and optional water-phase antioxidant, glidant, flavoring agent and coloring agent are dispersed in water, and the above components can be dispersed in water in any order. In some embodiments, the dispersion method comprises dissolving the water-phase wall material in water at 35° C. to 45° C., and ultrasonically dispersing it under an inert atmosphere to obtain a wall material aqueous solution, and the condition for the ultrasonic dispersion comprises an ultrasonic power of 240 w to 480 w, an ultrasonic time of 10 to 30 min, the solution passed through an ultrasonic probe in a countercurrent circulation mode, and then the part of vitamin E-polyethylene glycol succinate and optional water-phase antioxidant, glidant, flavoring agent and coloring agent are added into the wall material aqueous solution and mixed evenly under an inert atmosphere to obtain the water-phase material.

In a specific embodiment, in step (1), the vitamin K2, polyunsaturated fatty acid source, the remaining vitamin E-polyethylene glycol succinate and optional oil-phase antioxidant are uniformly mixed by a method that the vitamin K2, polyunsaturated fatty acid source, vitamin E-polyethylene glycol succinate and optional oil-phase antioxidant are heated to 35° C. to 50° C., kept warm and stirred until all components are completely dissolved to obtain the oil-phase material.

In a specific embodiment, in step (2), the water-phase material and the oil-phase material are mixed by a method that the water-phase material and the oil-phase material are simultaneously discharged at a mass ratio of (1.5 to 2.5):1.

In a specific embodiment, in step (2), the spray-drying is performed under a condition comprising a spray inlet air temperature of 140° C. to 170° C., an air outlet temperature of 80° C. to 95° C., an atomizer frequency of 165 to 200 Hz, a cooling air temperature of 16° C. to 22° C., and a feed temperature of 50° C. to 60° C.

The present disclosure also provides a vitamin K2 microcapsule as prepared by the above method.

The present disclosure also provides use of the vitamin K2 microcapsule as a dietary supplement or a health food.

In addition, the present disclosure also provides use of the vitamin K2 microcapsule in the manufacture of a medicament for preventing or treating cardiovascular and cerebrovascular diseases. The vitamin K2 microcapsule has significant effects in preventing or treating cardiovascular and cerebrovascular diseases. The cardiovascular and cerebrovascular diseases include hypertension, hyperlipidemia, myocardial infarction, atherosclerosis, cerebral infarction and the like. Among them, hyperlipidemia includes hypercholesterolemia, hypertriglyceridemia, etc., which are specifically manifested as one or more of the followings: an increase in total cholesterol, an increase in low-density lipoprotein cholesterol, an increase in triglycerides, and a decrease in high-density lipoprotein cholesterol in the blood.

Hereinafter, the present disclosure is described in detail through examples.

EXAMPLE 1

(1) Composition of Raw Materials:

| Component | Feeding amount (parts by weight) |
|---|---|
| Vitamin K2 | 0.005 |
| Linseed oil | 5 |
| Soybean oil | 4 |
| Grape seed oil | 1 |
| TPGS | 0.5 (0.4 in water-phase, 0.1 in oil-phase) |
| Rosemary extract | 0.03 |
| Sodium ascorbate | 0.02 |
| Modified starch capsul TA | 25 |
| Solid corn syrup | 30 |
| Maltodextrin | 34.445 |

In the above-mentioned mixed oil composed of linseed oil, soybean oil and grape seed oil, the polyunsaturated fatty acids ω-6/ω-3 had a weight ratio of 1.5:1.

(2) Preparation of Vitamin K2 Microcapsule:

The modified starch, solid corn syrup and maltodextrin were dissolved in 110 parts by weight of pure water at 40° C., and ultrasonically treated in a nitrogen atmosphere, in which the ultrasonic power was 240 w, the ultrasonic treatment time was 30 min, the material liquid passed through an ultrasonic probe in a countercurrent circulation mode to obtain a wall material aqueous solution; then sodium ascorbate and 0.4 parts by weight of TPGS were added to the obtained wall material aqueous solution, dissolved and mixed uniformly in a nitrogen atmosphere to prepare a water-phase material. The vitamin K2, linseed oil, soybean oil, grape seed oil, 0.1 parts by weight of TPGS, and rosemary extract were heated to 40° C. under a nitrogen atmosphere, kept warm and stirred until the components were completely dissolved to obtain an oil-phase material. Then, the obtained water-phase material and oil-phase material were simultaneously discharged at a speed ratio of 2:1 and mixed, sheared for 10 minutes at a rotational speed of 10,000 rpm to emulsify the system to achieve an oil droplet size of ≤2 microns, and then entered into a high pressure micro-jet with a set pressure of 30 MPa and treated twice to obtain an emulsion with an oil droplet size of ≤100 nanometers; the obtained emulsion was subjected to spray-drying with a feed temperature of 50° C., an inlet air temperature of 150° C., an outlet air temperature of 80° C., an atomizer frequency of 180 Hz and a cooling air temperature of 22° C., so as to obtain vitamin K2 microcapsules with a yield of 98.7% (calculated with vitamin K2, the same below), in which the content of vitamin K2 was 4957 ppm, and the oil droplet size distribution $D_{90}$ was 92 nm.

EXAMPLE 2

(1) Composition of Raw Materials:

| Component | Feeding amount (parts by weight) |
|---|---|
| Vitamin K2 | 0.005 |
| Perilla seed oil | 5 |
| Walnut oil | 2 |
| Low erucic acid rapeseed oil | 3 |
| TPGS | 1 (0.8 in water-phase, 0.2 in oil-phase) |
| Sodium ascorbate | 0.02 |
| Ascorbyl palmitate | 0.03 |
| Modified starch capsul TA | 30 |
| Dry glucose syrup powder | 25 |
| Maltodextrin | 33.945 |

In the above-mentioned mixed oil composed of perilla seed oil, walnut oil and low erucic acid rapeseed oil, the polyunsaturated fatty acids ω-6/ω-3 had a weight ratio of 0.8:1.

(2) Preparation of Vitamin K2 Microcapsule:

The modified starch, dry glucose syrup powder, and maltodextrin were dissolved in 110 parts by weight of pure water at 40° C., and ultrasonically treated in a nitrogen atmosphere, in which the ultrasonic power was 300 w, and the ultrasonic treatment time was 25 min, the material liquid passed through an ultrasonic probe in a countercurrent circulation mode to obtain a wall material aqueous solution; then sodium ascorbate and 0.8 parts by weight of TPGS were added to the obtained wall material aqueous solution, dissolved and mixed uniformly under a nitrogen atmosphere to prepare a water-phase material. The vitamin K2, perilla oil, walnut oil, low erucic acid rapeseed oil, 0.2 parts by weight of TPGS, and ascorbyl palmitate were heated to 45° C. under a nitrogen atmosphere, kept warm and stirred until the components were completely dissolved to obtain an oil-phase material. Then, the obtained water-phase solution and oil-phase materials were simultaneously discharged at a speed ratio of 2:1 and mixed, sheared at a rotational speed of 10000 rpm for 10 minutes to emulsify the system to achieve an oil droplet size of ≤2 microns, and then entered into a high pressure micro-jet with a set pressure of 35 MPa and treated twice to obtain an emulsion with an oil droplet size of ≤100 nanometers; the obtained emulsion was subjected to spray-drying with a feed temperature of 50° C., an inlet air temperature of 160° C., an outlet air temperature of 80° C., an atomizer frequency of 180 Hz and a cooling air temperature of 18° C. to obtain vitamin K2 microcapsules with a yield of 99.0%, in which the content of vitamin K2 was 4965 ppm, and the oil droplet size distribution $D_{90}$ was 90 nm.

EXAMPLE 3

(1) Composition of Raw Materials:

| Component | Feeding amount (parts by weight) |
|---|---|
| Vitamin K2 | 0.005 |
| DHA algae oil | 2 |
| Fish oil | 2 |
| ARA oil | 6 |
| TPGS | 1 (0.8 in water-phase, 0.2 in oil-phase) |
| Sodium ascorbate | 0.01 |
| Sodium citrate | 0.01 |
| Rosemary extract | 0.02 |
| Lecithin | 0.02 |
| Whey protein | 35 |
| White granulated sugar | 20 |
| Maltodextrin | 33.935 |

In the above-mentioned mixed oil composed of DHA algae oil, fish oil and ARA oil, the polyunsaturated fatty acids ω-6/ω-3 had a weight ratio of 2.5:1.

(2) Preparation of Vitamin K2 Microcapsule:

The whey protein, white granulated sugar, and maltodextrin were mixed in 120 parts by weight of pure water at 45° C., and ultrasonically treated in a nitrogen atmosphere, in which the ultrasonic power was 480 w, the ultrasonic treatment time was 10 min, the material liquid passed through an ultrasonic probe in a countercurrent circulation mode to obtain a wall material aqueous solution; then sodium ascorbate, sodium citrate and 0.8 parts by weight of TPGS were added to the obtained wall material aqueous solution, dissolved and mixed uniformly under a nitrogen atmosphere to obtain a water-phase material. The vitamin K2, DHA algae oil, fish oil, ARA oil, 0.2 parts by weight of TPGS, rosemary extract, and lecithin were heated to 45° C. under a nitrogen atmosphere, kept warm and stirred until all component were completely dissolved to obtain an oil-phase material. Then, the obtained water-phase material and oil-phase material were simultaneously discharged at a speed ratio of 2:1 and mixed, sheared at a rotational speed of 10000 rpm for 10 minutes to emulsify the system to achieve an oil droplet size of ≤2 microns, and then entered into a high-pressure micro-jet with a set pressure of 30 MPa and treated twice to obtain an emulsion with an oil droplet size of ≤100 nanometers; the obtained emulsion was subjected to spray-drying with a feed temperature of 50° C., an inlet air temperature of 155° C., an outlet air temperature of 85° C., an atomizer frequency of 180 Hz, and a cooling air temperature of 18° C. to obtain vitamin K2 microcapsules with a yield of 98.9%, in which the content of vitamin K2 was 4958 ppm, and the oil droplet size distribution $D_{90}$ was 89 nm.

EXAMPLE 4

(1) Composition of Raw Materials:

| Component | Feeding amount (parts by weight) |
|---|---|
| Vitamin K2 | 0.005 |
| Walnut oil | 4 |
| Linseed oil | 1 |
| Sesame oil | 4 |
| Perilla seed oil | 1 |
| TPGS | 1.5 (1.2 in water-phase, 0.3 in oil-phase) |
| Sodium ascorbate | 0.02 |
| Rosemary extract | 0.02 |
| Ascorbyl palmitate | 0.02 |
| Arabic gum SD | 35 |
| Arabic gum FT | 18 |
| White granulated sugar | 12 |
| Maltodextrin | 23.435 |

In the above-mentioned mixed oil composed of walnut oil, linseed oil, sesame oil and perilla seed oil, the polyunsaturated fatty acids ω-6/ω-3 had a weight ratio of 3.5:1.

(2) Preparation of Vitamin K2 Microcapsule:

The Arabic gum SD, Arabic gum FT, white granulated sugar, and maltodextrin were dissolved in 110 parts by weight of pure water at 45° C., and ultrasonically treated in a nitrogen atmosphere, in which the ultrasonic power was 350 w, the ultrasonic treatment time was 20 min, the material liquid passed through an ultrasonic probe in a countercurrent circulation mode to obtain a wall material aqueous solution; then sodium ascorbate and 1.2 parts by weight of TPGS were added to the obtained wall material aqueous solution, dissolved and mixed uniformly in a nitrogen atmosphere to prepare a water-phase material. The vitamin K2, walnut oil, linseed oil, sesame oil, perilla oil, 0.3 parts by weight of TPGS, rosemary extract, and ascorbyl palmitate were heated under a nitrogen atmosphere to 45° C., kept warm and stirred until the components were completely dissolved to obtain an oil-phase material. Then, the obtained water-phase material and oil-phase material were simultaneously discharged at a speed ratio of 2:1 and mixed, sheared at a rotational speed of 10000 rpm for 10 minutes to emulsify the system to achieve an oil droplet size of ≤2 microns, and then entered into a high pressure micro-jet with a set pressure of 40 MPa and treated twice to obtain an emulsion with an oil droplet size of ≤100 nanometers; the obtained emulsion was subjected to spray-drying with a feed temperature of 55° C., an inlet air temperature of 165° C., an outlet air temperature of 85° C., an atomizer frequency of 185 Hz and a cooling air temperature of 18° C. to obtain vitamin K2 microcapsules with a yield of 99.2%, in which the content of vitamin K2 was 4971 ppm, and the oil droplet size distribution $D_{90}$ was 86 nm.

EXAMPLE 5

(1) Composition of Raw Materials:

| Component | Feeding amount (parts by weight) |
|---|---|
| Vitamin K2 | 10 |
| Fish oil | 5 |
| DHA algae oil | 5 |
| Sunflower seed oil | 20 |
| TPGS | 5 (4 in water-phase, 1 in oil-phase) |
| Sodium ascorbate | 2 |
| Ascorbyl palmitate | 3 |
| Modified starch 12633 | 25 |
| Solid corn syrup | 15 |
| Maltodextrin | 10 |

In the above-mentioned mixed oil composed of fish oil, DHA algae oil, and sunflower seed oil, the polyunsaturated fatty acids ω-6/ω-3 had a weight ratio of 2.1:1.

(2) Preparation of Vitamin K2 Microcapsule:

The modified starch, solid corn syrup, and maltodextrin were dissolved in 120 parts by weight of pure water at 40° C., and ultrasonically treated in a nitrogen atmosphere, in which the ultrasonic power was 480 w, the ultrasonic treatment time was 10 min, the material liquid passed through an ultrasonic probe in a countercurrent circulation mode to obtain a wall material aqueous solution; then sodium ascorbate and 4 parts by weight of TPGS were added to the obtained wall material aqueous solution, dissolved and mixed uniformly in a nitrogen atmosphere to prepare a water-phase material. The vitamin K2, fish oil, DHA algae oil, sunflower seed oil, 1 part by weight of TPGS, and ascorbyl palmitate were heated to 45° C. under a nitrogen atmosphere, kept warm and stirred until the components were completely dissolved to obtain an oil-phase material. Then the obtained water-phase material and oil-phase material were simultaneously discharged at a speed ratio of 2:1 and mixed, sheared at a rotational speed of 10000 rpm for 15 minutes to emulsify the system to achieve an oil droplet size of ≤2 microns, and then entered into a high pressure micro-jet with a set pressure of 50 MPa and treated twice to obtain an emulsion with an oil droplet size of ≤100 nanometers; the obtained emulsion was subjected to spray-drying with a feed temperature of 55° C., an inlet air temperature of 170° C., an outlet air temperature of 95° C., an atomizer frequency of 180 Hz and a cooling air temperature of 16° C. to obtain vitamin K2 microcapsules with a yield of 99.1%, in which the content of vitamin K2 was 9.94%, and the oil droplet size distribution $D_{90}$ was 93 nm.

EXAMPLE 6

(1) Composition of Raw Materials:

| Component | Feeding amount (parts by weight) |
| --- | --- |
| Vitamin K2 | 10 |
| Perilla seed oil | 5 |
| Safflower seed oil | 15 |
| TPGS | 5 (4 in water-phase, 1 in oil-phase) |
| Sodium ascorbate | 2 |
| Ascorbyl palmitate | 3 |
| Modified starch T809 | 12 |
| Arabic gum SD | 18 |
| White granulated sugar | 13 |
| Maltodextrin | 17 |

In the above-mentioned mixed oil composed of perilla seed oil and safflower seed oil, the polyunsaturated fatty acids ω-6/ω-3 had a weight ratio of 4.0:1.

(2) Preparation of Vitamin K2 Microcapsule:

The modified starch, Arabic gum SD, white granulated sugar, and maltodextrin were dissolved in 110 parts by weight of pure water at 40° C., and ultrasonically treated in a nitrogen atmosphere, in which the ultrasonic power was 300 w, the ultrasonic treatment time was 25 min, the material liquid passed through an ultrasonic probe in a countercurrent circulation mode to obtain a wall material aqueous solution; then sodium ascorbate and 4 parts by weight of TPGS were added to the obtained wall material aqueous solution, dissolved and mixed uniformly in a nitrogen atmosphere to prepare an water-phase material. The vitamin K2, perilla seed oil, safflower seed oil, 1 part by weight of TPGS, and ascorbyl palmitate were heated to 45° C. under a nitrogen atmosphere, kept warm and stirred until the components were completely dissolved to obtain an oil-phase material. Then the obtained water-phase material and oil-phase material were simultaneously discharged at a speed ratio of 2:1 and mixed, sheared at a rotational speed of 10000 rpm for 15 minutes to emulsify the system to achieve an oil droplet size of ≤2 microns, and then entered into a high pressure micro-jet with a set pressure of 50 MPa and treated twice to obtain an emulsion with an oil droplet size of ≤100 nanometers; the obtained emulsion was subjected to spray-drying with a feed temperature of 55° C., an inlet air temperature of 170° C., an outlet air temperature of 85° C., an atomizer frequency of 185 Hz and a cooling air temperature of 20° C. to obtain vitamin K2 microcapsules with a yield of 98.8%, in which the content of vitamin K2 was 9.91%, and the oil droplet size distribution $D_{90}$ was 96 nm.

EXAMPLE 7

(1) Composition of Raw Materials:

| Component | Feeding amount (parts by weight) |
| --- | --- |
| Vitamin K2 | 1 |
| Zanthoxylum seed oil | 8 |
| Linseed oil | 2 |
| Sunflower seed oil | 10 |
| TPGS | 2 (1.6 in water-phase, 0.4 in oil-phase) |
| Sodium ascorbate | 2 |
| Ascorbyl palmitate | 1 |
| Rosemary extract | 1 |
| Arabic gum SD | 24 |
| Arabic gum FT | 20 |
| White granulated sugar | 13 |
| Maltodextrin | 16 |

In the above-mentioned mixed oil composed of zanthoxylum seed oil, linseed oil and sunflower seed oil, the polyunsaturated fatty acids ω-6/ω-3 had a weight ratio of 3.1:1.

(2) Preparation of Vitamin K2 Microcapsule:

The Arabic gum SD, Arabic gum FT, white granulated sugar, and maltodextrin were dissolved in 110 parts by weight of pure water at 45° C., and ultrasonically treated in a nitrogen atmosphere, in which the ultrasonic power was 350 w, the ultrasonic treatment time was 20 min, the material liquid passed through an ultrasonic probe in a countercurrent circulation mode to obtain a wall material aqueous solution; then sodium ascorbate and 1.6 parts by weight of TPGS were added to the obtained wall material aqueous solution, dissolved and mixed uniformly in a nitrogen atmosphere to prepare an aqueous phase material. The vitamin K2, zanthoxylum seed oil, linseed oil, sunflower seed oil, 0.4 parts by weight of TPGS, rosemary extract, and ascorbyl palmitate were heated under a nitrogen atmosphere to 40° C., kept warm and stirred until the components were completely dissolved to obtain an oil-phase material. Then, the obtained water-phase material and oil-phase material were simultaneously discharged at a speed ratio of 2:1 and mixed, sheared at a rotational speed of 10000 rpm for 10 minutes to emulsify the system to achieve an oil droplet size of ≤2 microns, and then entered into a high pressure micro-jet with a set pressure of 40 MPa and treated twice to obtain an emulsion with an oil droplet size of ≤100 nanometers; the obtained emulsion was subjected to spray-drying with a feed temperature of 50° C., an inlet air temperature of 165° C., an outlet air temperature of 90° C., an atomizer frequency of 190 Hz and a cooling air temperature of 20° C. to obtain vitamin K2 microcapsules with a yield of 99.2%, in which the content of vitamin K2 was 0.99%, and the oil droplet size distribution $D_{90}$ was 81 nm.

EXAMPLE 8

(1) Composition of Raw Materials:

| Component | Feeding amount (parts by weight) |
|---|---|
| Vitamin K2 | 1 |
| DHA algae oil | 5 |
| Walnut oil | 2 |
| Grape seed oil | 10 |
| Soybean oil | 3 |
| TPGS | 3 (2.4 in water-phase, 0.6 in oil phase) |
| Sodium ascorbate | 2 |
| Sodium citrate | 1 |
| Lecithin | 3 |
| Gliadin | 38 |
| Solid corn syrup | 20 |
| Maltodextrin | 12 |

In the above-mentioned mixed oil composed of DHA algae oil, walnut oil, grape seed oil, and soybean oil, the polyunsaturated fatty acids ω-6/ω-3 had a weight ratio of 1.7:1.

(2) Preparation of Vitamin K2 Microcapsule:

The gliadin, solid corn syrup, and maltodextrin were dissolved in 110 parts by weight of pure water at 40° C., and ultrasonically treated in a nitrogen atmosphere, in which the ultrasonic power was 400 w, the ultrasonic treatment time was 25 min, the material liquid passed through an ultrasonic probe in a countercurrent circulation mode to obtain a wall material aqueous solution; then sodium ascorbate, sodium citrate, and 2.4 parts by weight of TPGS were added to the obtained wall material aqueous solution, dissolved and mixed uniformly in a nitrogen atmosphere to prepare a water-phase material. The vitamin K2, DHA algae oil, walnut oil, grape seed oil, soybean oil, 0.6 parts by weight of TPGS, and lecithin were heated to 45° C. under a nitrogen atmosphere, kept warm and stirred until all components were completely dissolved to obtain an oil-phase material. Then the obtained water-phase material and oil-phase material were simultaneously discharged at a speed ratio of 2:1 and mixed, sheared for 15 minutes at a rotational speed of 10,000 rpm to emulsify the system to achieve an oil droplet size of ≤2 microns, and then entered into a high pressure micro-jet with a set pressure of 40 MPa and treated twice to obtain an emulsion with an oil droplet size of ≤100 nanometers; the obtained emulsion was subjected to spray-drying with a feed temperature of 50° C., an inlet air temperature of 165° C., an outlet air temperature of 90° C., an atomizer frequency of 185 Hz and a cooling air temperature of 20° C. to obtain vitamin K2 microcapsules with a yield of 98.9%, in which the content of vitamin K2 was 0.99%, and the oil droplet size distribution $D_{90}$ was 87 nm.

EXAMPLE 9

(1) Composition of Raw Materials:

| Component | Feeding amount (parts by weight) |
|---|---|
| Vitamin K2 | 5 |
| Perilla oil | 6 |
| ARA oil | 2 |
| Sesame oil | 3 |
| Soybean oil | 4 |
| Sunflower seed oil | 5 |
| TPGS | 3 (2.4 in water-phase, 0.6 in oil-phase) |
| Sodium ascorbate | 2 |
| Rosemary extract | 1 |
| Natural VE | 1 |
| Arabic gum SD | 25 |
| Arabic gum FT | 18 |
| Solid corn syrup | 10 |
| Maltodextrin | 15 |

In mixed oil composed of perilla oil, ARA oil, sesame oil, soybean oil and sunflower seed oil, the polyunsaturated fatty acids ω-6/ω-3 had a weight ratio of 2.4:1.

(2) Preparation of Vitamin K2 Microcapsule:

The Arabic gum SD, Arabic gum FT, solid corn syrup, and maltodextrin were dissolved in 110 parts by weight of pure water at 45° C., and ultrasonically treated in a nitrogen atmosphere, in which the ultrasonic power was 350 w, the ultrasonic treatment time was 25 min, the material liquid passed through an ultrasonic probe in a countercurrent circulation mode to obtain a wall material aqueous solution; then sodium ascorbate and 2.4 parts by weight of TPGS were added to the obtained wall material aqueous solution, dissolved and mixed uniformly under a nitrogen atmosphere to prepare a water-phase material. The vitamin K2, perilla oil, ARA oil, sesame oil, soybean oil, sunflower seed oil, 0.6 parts by weight of TPGS, rosemary extract, and natural VE were heated under a nitrogen atmosphere to 45° C., kept warm and stirred until the components were completely dissolved to obtain an oil-phase material. Then, the obtained water-phase material and oil-phase material were simultaneously discharged at a speed ratio of 2:1 and mixed, sheared for 15 minutes at a rotational speed of 10,000 rpm to emulsify the system to achieve an oil droplet size of ≤2 microns, and then entered into a high pressure micro-jet with a set pressure of 45 MPa and treated twice to obtain an emulsion with an oil droplet size of ≤100 nanometers; the obtained emulsion was subjected to spray-drying with a feed temperature of 55° C., an inlet air temperature of 170° C., an outlet air temperature of 85° C., an atomizer frequency of 180 Hz and a cooling air temperature of 22° C. to obtain vitamin K2 microcapsules with a yield of 98.9%, in which the content of vitamin K2 was 4.94%, and the oil droplet size distribution $D_{90}$ was 89 nm.

EXAMPLE 10

(1) Composition of Raw Materials:

| Component | Feeding amount (parts by weight) |
|---|---|
| Vitamin K2 | 5 |
| DHA algae oil | 10 |
| ARA oil | 15 |
| TPGS | 5 (4 in water-phase, 1 in oil-phase) |
| Sodium ascorbate | 2 |
| Rosemary extract | 1 |
| Ascorbyl palmitate | 2 |
| Modified starch capsul TA | 25 |
| Solid corn syrup | 18 |
| Maltodextrin | 17 |

In the above-mentioned mixed oil composed of DHA algae oil and ARA oil, the polyunsaturated fatty acids ω-6/ω-3 had a weight ratio of 1.5:1.

(2) Preparation of Vitamin K2 Microcapsule:

The modified starch, solid corn syrup, and maltodextrin were dissolved in 110 parts by weight of pure water at 45°

C., and ultrasonically treated in a nitrogen atmosphere, in which the ultrasonic power was 300 w, the ultrasonic treatment time was 30 min, the material liquid passed through an ultrasonic probe in a countercurrent circulation mode to obtain a wall material aqueous solution; then sodium ascorbate and 4 parts by weight of TPGS were added to the obtained wall material aqueous solution, dissolved and mixed uniformly in a nitrogen atmosphere to prepare a water-phase material. The vitamin K2, DHA algae oil, ARA oil, 1 part by weight of TPGS, rosemary extract, and ascorbyl palmitate were heated to 40° C. under a nitrogen atmosphere, kept warm and stirred until all components were completely dissolved to obtain an oil-phase material. Then, the obtained water-phase material and oil-phase material were simultaneously discharged at a speed ratio of 2:1 and mixed, sheared at a rotational speed of 10000 rpm for 10 minutes to emulsify the system to achieve an oil droplet size of ≤2 microns, and then entered into a high pressure microjet with a set pressure of 50 MPa and treated twice to obtain an emulsion with an oil droplet size of ≤100 nanometers; the obtained emulsion was subjected to spray-drying with a feed temperature of 50° C., an inlet air temperature of 170° C., an outlet air temperature of 90° C., an atomizer frequency of 180 Hz and a cooling air temperature of 16° C. to obtain vitamin K2 microcapsules with a yield of 99.0%, in which the content of vitamin K2 was 4.97%, and the oil droplet size distribution $D_{90}$ was 85 nm.

EXAMPLE 11

Vitamin K microcapsules were prepared according to the method of Example 1, except that the dosages of linseed oil, soybean oil and grape seed oil were adjusted to 8 parts by weight, 1 part by weight and 1 part by weight, respectively, so that the polyunsaturated fatty acids ω-6/ω-3 in the oil had a weight ratio of 0.2:1, and other conditions were the same as in Example 1, the obtained reference vitamin K2 microcapsules had a yield of 98.9%, in which the content of vitamin K2 was 4959 ppm, and the oil droplet size distribution $D_{90}$ was 91 nm.

EXAMPLE 12

Vitamin K microcapsules were prepared according to the method of Example 1, except that the dosages of linseed oil, soybean oil and grape seed oil were adjusted to 2 parts by weight, 2 parts by weight and 6 parts by weight, respectively, so that the polyunsaturated fatty acids ω-6/ω-3 in the oil had a weight ratio of 5:1, and the other conditions were the same as in Example 1. The obtained reference vitamin K2 microcapsules had a yield of 98.6%, in which the content of vitamin K2 was 4955 ppm, and the oil droplet size distribution $D_{90}$ was 94 nm.

COMPARATIVE EXAMPLE 1

In Comparative Example 1, the formula composition was the same as that of Example 1, and the preparation steps were the same as those of Example 1 except that all TPGS was added to the water-phase. The obtained reference vitamin K2 microcapsules had a yield of 94.3%, in which the content of vitamin K2 was 4912 ppm, and the oil droplet size distribution $D_{90}$ was 183 nm.

COMPARATIVE EXAMPLE 2

In Comparative Example 2, the formula composition was the same as that of Example 1, and the preparation steps were the same as those of Example 1 except that all TPGS was added to the oil-phase. The obtained reference vitamin K2 microcapsules had a yield of 94.1%, in which the content of vitamin K2 was 4906 ppm, and the oil droplet size distribution $D_{90}$ was 167 nm.

COMPARATIVE EXAMPLE 3

Vitamin K2 microcapsules were prepared according to the method of Example 1, except that TPGS was replaced with the same parts by weight of monoglyceride laurate, and the other conditions were the same as in Example 1. The obtained reference vitamin K2 microcapsules had a yield of 91.2%, in which the content of vitamin K2 was 4869 ppm, and the oil droplet size distribution $D_{90}$ was 202 nm.

COMPARATIVE EXAMPLE 4

Vitamin K2 microcapsules were prepared according to the method of Example 1, except that the polyunsaturated fatty acid source (linseed oil, soybean oil, grape seed oil) was replaced with the same parts by weight of MCT (medium chain triglyceride, saturated fatty acid), and the other conditions were the same as in Example 1. The obtained reference vitamin K2 microcapsules had a yield of 98.8%, in which the content of vitamin K2 was 4957 ppm, and the oil droplet particle size distribution $D_{90}$ was 93 nm.

COMPARATIVE EXAMPLE 5

Vitamin K2 microcapsules were prepared according to the method of Example 1, except that the vitamin K2 was replaced with the same parts by weight of MCT (medium chain triglyceride, saturated fatty acid), and the other conditions were the same as in Example 1. The obtained reference vitamin K2 Microcapsules had an oil droplet size distribution $D_{90}$ of 89 nm.

TEST EXAMPLE 1

Determination of Stability of Vitamin K2 Microcapsules (1) Samples
　Sample 1: Example 1;
　Sample 2: Example 11;
　Sample 3: Example 12;
　Reference sample 1: Comparative Example 1;
　Reference sample 2: Comparative Example 2;
　Reference sample 3: Comparative Example 3;
　Reference sample 4: Vitamin K2 (VK2), raw material.

(2) Test Method

The samples and the reference samples were respectively put into sealed colorless and transparent vials, and placed under the conditions of 4500Lx light intensity irradiation, oxygen filling (25° C.), and stored at 60° C. (incubator) for 15 days, respectively; and they were subjected to sampling on Day 0, Day 5, Day 10, Day 15, and VK2 contents thereof were determined by USP method. The effects of light, oxygen, and temperature conditions on the labeled content (%) of VK2 were investigated. The results were shown in Table 1.

TABLE 1

Effects of light, oxygen and temperature conditions on the stability of VK2

| Experimental conditions | Test item | Sample | Day 0 | Day 5 | Day 10 | Day 15 |
|---|---|---|---|---|---|---|
| 4500 Lx illumination | Labeled content of VK2 (%) | Sample 1 | 100.0% | 99.8% | 99.0% | 98.5% |
| | | Sample 2 | 100.0% | 99.9% | 99.1% | 98.6% |
| | | Sample 3 | 100.0% | 99.8% | 99.0% | 98.4% |
| | | Reference sample 1 | 100.0% | 97.2% | 95.3% | 93.1% |
| | | Reference sample 2 | 100.0% | 97.0% | 94.4% | 92.7% |
| | | Reference sample 3 | 100.0% | 95.1% | 92.2% | 89.7% |
| | | Reference sample 4 | 100.0% | 89.2% | 74.3% | 60.3% |
| Oxygen filling (25° C.) | Labeled content of VK2 (%) | Sample 1 | 100.0% | 100.0% | 99.7% | 99.2% |
| | | Sample 2 | 100.0% | 100.0% | 99.8% | 99.3% |
| | | Sample 3 | 100.0% | 100.0% | 99.6% | 99.2% |
| | | Reference sample 1 | 100.0% | 98.3% | 96.7% | 94.7% |
| | | Reference sample 2 | 100.0% | 98.6% | 97.5% | 95.1% |
| | | Reference sample 3 | 100.0% | 96.7% | 92.6% | 90.1% |
| | | Reference sample 4 | 100.0% | 93.5% | 89.4% | 81.2% |
| 60° C. (incubator) | Labeled content of VK2 (%) | Sample 1 | 100.0% | 100.0% | 99.8% | 99.0% |
| | | Sample 2 | 100.0% | 100.0% | 99.8% | 99.1% |
| | | Sample 3 | 100.0% | 100.0% | 99.8% | 98.9% |
| | | Reference sample 1 | 100.0% | 99.5% | 98.4% | 97.3% |
| | | Reference sample 2 | 100.0% | 99.7% | 98.5% | 97.4% |
| | | Reference sample 3 | 100.0% | 97.9% | 95.6% | 93.7% |
| | | Reference sample 4 | 100.0% | 96.2% | 94.8% | 90.4% |

The results in Table 1 showed that the vitamin K2 microcapsules prepared by the present disclosure had basically no change in the labeled content of VK2 under the conditions of accelerated aging under light, oxygen and high temperature, and there was no obvious damage to VK2, indicating that the vitamin K2 microcapsules prepared by the present disclosure had good stability, could reduce the influence of light, oxygen and high temperature on its properties, and the product had a good shelf life.

TEST EXAMPLE 2

Determination of Water Dispersibility and Solubility of Vitamin K2 Microcapsules (1) Samples The vitamin K2 microcapsules prepared in Examples 1 to 12 (codes: Y1, Y2, Y3, Y4, Y5, Y6, Y7, Y8, Y9, Y10, Y11, Y12);

Reference substance 1 (code: DY1): 2000 ppm water-soluble vitamin K2 microcapsules purchased from a biotechnology company in Shanghai;

Reference substance 2 (code: DY2): 2000 ppm water-soluble vitamin K2 microcapsules purchased from a pharmaceutical technology company in Guangdong;

Reference substance 3 (code: DY3): Reference vitamin K2 microcapsule prepared in Comparative Example 1;

Reference substance 4 (code: DY4): Reference vitamin K2 microcapsule prepared in Comparative Example 2;

Reference substance 5 (code: DY5): Reference vitamin K2 microcapsule prepared in Comparative Example 3;

Reference substance 6 (code: DY6): Reference vitamin K2 microcapsule prepared in Comparative Example 4;

Reference substance 7 (code: DY7): Reference vitamin K2 microcapsule prepared in Comparative Example 5.

(2) Test Method

At room temperature, 50 mL of 25° C. water was added to a 100 mL beaker, allowed to stand until there was no bubble in the water and the water surface was stable; then 1.00 g of each of the samples and the reference substances was taken, and quickly poured into the water from the same position above the center of the beaker, and the time of dispersion and dissolution in water, that was, the time that the sample was completely wetted and sank to the bottom of the beaker, was recorded. The results were shown in Table 2. The results in Table 2 showed that the vitamin K2 microcapsules obtained in the present disclosure could be quickly dispersed and dissolved in water, and had good water dispersibility.

TABLE 2

Time of dispersion and dissolution of each sample microcapsule in water

| Item | Y1 | Y2 | Y3 | Y4 | Y5 | Y6 | Y7 | Y8 | Y9 | Y10 | Y11 | Y12 |
|---|---|---|---|---|---|---|---|---|---|---|---|---|
| Time(s) | 15 | 12 | 12 | 14 | 20 | 22 | 18 | 16 | 17 | 20 | 16 | 15 |
| Item | DY1 | DY2 | DY3 | DY4 | DY5 | DY6 | DY7 | — | — | — | — | — |
| Time(s) | 92 | 134 | 35 | 31 | 56 | 16 | 13 | — | — | — | — | — |

TEST EXAMPLE 3

Blood Lipid-Reducing Function Test of Vitamin K2 Microcapsules (1) Principle

Feeding animals with diets high in cholesterol and lipid could form an animal model of lipid metabolism disorder, and then administrating the animals with a test sample, the effect of the test sample on hyperlipidemia could be detected, and the effects of the test sample on the absorption of lipid and lipoprotein as well as the degradation or excretion of lipid could be determined.

(2) Instruments and Reagents

Dissecting equipment, spectrophotometer, automatic biochemical analyzer, kits for determination of cholesterol, bile salts, serum total cholesterol (TC), triglycerides (TG), and high-density lipoprotein cholesterol (HDL-C).

(3) Animal Selection and Feed

Healthy adult male SD rats, weighing 150-200 g, were selected, and randomly divided every 10 rats into a group by using completely random design.

High-fat diet group: 78.8 wt % basic feed, 1 wt % cholesterol, 10 wt % protein powder, 10 wt % lard, and 0.2 wt % bile salt.

Standard diet group: basic feed.

(4) Sample

Sample 1: Vitamin K2 microcapsule prepared in Example 1;
Sample 2: Vitamin K2 microcapsule prepared in Example 2;
Sample 3: Vitamin K2 microcapsule prepared in Example 3;
Sample 4: Vitamin K2 microcapsule prepared in Example 4;
Sample 5: Vitamin K2 microcapsule prepared in Example 11;
Sample 6: Vitamin K2 microcapsule prepared in Example 12;
Reference substance 1: Vitamin K2 microcapsule prepared in Comparative Example 4.
Reference substance 2: Vitamin K2 microcapsule prepared in Comparative Example 5.

(5) Method

In the experiment, 10 groups were set, in which Group 1 was a high-fat diet control group (given a high-fat diet), Group 2 was a standard diet group (given a standard diet), and the other groups were given a high-fat diet every day and simultaneously administrated by oral gavage with vitamin K2 microcapsules prepared from the samples 1 to 6 and the reference substances 1 to 2, 3 times a day, and the test time was 30 days.

(6) Experimental Steps

In the experimental environment, the rats were fed with basic feed and observed for 10 days, and then the tail blood was taken to determine the levels of serum total cholesterol (TC), triglyceride (TG), and high-density lipoprotein cholesterol (HDL-C). According to the TC levels, they were randomly divided into 10 groups. The sampling was performed according to the method described in (5) above, and the body weight was weighed regularly. After the end of test, fasting was performed for 16 hours and the levels of serum TC, TG and HDL-C were measured. The results were shown in Table 3.

TABLE 3

Test results of total cholesterol (mg/dL)

| Group | Diet | Total cholesterol (mg/dL), mean ± standard error | Decreased (%) | Student't test P< | VS |
|---|---|---|---|---|---|
| 1 | Control (high-fat diet) | 556.9 ± 24.3 | — | — | — |
| 2 | Standard diet | 224.8 ± 16.9 | 59 | 0.001 | Control group |
| 3 | Sample 1 | 179.4 ± 18.8 | 68 | 0.001 | Control group |
| 4 | Sample 2 | 215.3 ± 24.7 | 61 | 0.001 | Control group |
| 5 | Sample 3 | 220.1 ± 20.4 | 60 | 0.01 | Control group |
| 6 | Sample 4 | 240.8 ± 21.5 | 57 | 0.01 | Control group |
| 7 | Sample 5 | 367.5 ± 28.7 | 34 | 0.01 | Control group |
| 8 | Sample 6 | 356.1 ± 29.4 | 36 | 0.05 | Control group |
| 9 | Reference substance 1 | 442.7 ± 25.3 | 21 | 0.01 | Control group |
| 10 | Reference substance 2 | 454.8 ± 27.2 | 18 | 0.01 | Control group |

TABLE 4

Test results of serum triglyceride (TG)

| Group | Diet | Serum triglyceride (mg/dL), mean ± standard error | Decreased (%) | Student't test P< | VS |
|---|---|---|---|---|---|
| 1 | Control (high-fat diet) | 301.3 ± 17.6 | — | — | — |
| 2 | Standard diet | 67.8 ± 10.2 | 77 | 0.001 | Control group |
| 3 | Sample 1 | 121.8 ± 11.6 | 59 | 0.01 | Control group |
| 4 | Sample 2 | 147.2 ± 12.7 | 51 | 0.001 | Control group |
| 5 | Sample 3 | 159.1 ± 15.8 | 47 | 0.01 | Control group |
| 6 | Sample 4 | 166.8 ± 14.5 | 45 | 0.01 | Control group |
| 7 | Sample 5 | 233.6 ± 22.5 | 22 | 0.05 | Control group |
| 8 | Sample 6 | 245.9 ± 23.4 | 18 | 0.01 | Control group |
| 9 | Reference substance 1 | 256.8 ± 19.8 | 15 | 0.05 | Control group |
| 10 | Reference substance 2 | 277.3 ± 20.1 | 8 | 0.01 | Control group |

TABLE 5

Test results of serum high-density lipoprotein cholesterol (HDL-C)

| Group | Diet | Serum high-density lipoprotein cholesterol (mg/dL), mean ± standard error | Increased (%) | Student't test P< | VS |
|---|---|---|---|---|---|
| 1 | Control (high-fat diet) | 36.7 ± 14.9 | — | — | — |
| 2 | Standard diet | 49.5 ± 15.2 | 36 | 0.001 | Control group |
| 3 | Sample 1 | 53.7 ± 10.2 | 46 | 0.01 | Control group |
| 4 | Sample 2 | 52.2 ± 10.4 | 42 | 0.01 | Control group |
| 5 | Sample 3 | 50.7 ± 11.1 | 38 | 0.01 | Control group |
| 6 | Sample 4 | 48.8 ± 9.6 | 33 | 0.001 | Control group |
| 7 | Sample 5 | 42.9 ± 9.8 | 17 | 0.01 | Control group |
| 8 | Sample 6 | 41.8 ± 13.6 | 14 | NS | Control group |
| 9 | Reference substance 1 | 39.3 ± 14.9 | 7 | 0.01 | Control group |
| 10 | Reference substance 2 | 40.6 ± 16.4 | 10 | 0.05 | Control group |

From the results in Table 3 to Table 5, it could be seen that the vitamin K2 microcapsules prepared by the present disclosure could effectively reduce the levels of total cholesterol (TC) and triglycerides (TG) in rat serum, and could significantly elevate high-density lipoprotein cholesterol (HDL-C) level.

Although the examples of the present disclosure have been shown and described above, it can be understood that the above examples are exemplary and should not be construed as limiting the present disclosure. Those of ordinary skill in the art will able to change, modify, substitute and alter the above examples within the scope of the present disclosure without departing from the principle and purpose of the present disclosure.

What is claimed is:

1. A method for preparing vitamin K2 microcapsule, wherein the vitamin K2 microcapsule comprises the following components by weight: 0.001 to 10 parts of vitamin K2, 5 to 30 parts of polyunsaturated fatty acid source, 0.1 to 10 parts of vitamin E-polyethylene glycol succinate, 50 to 95 parts of water-phase wall material wherein the water-phase wall material is at least one selected from the group consisting of protein compound wall material, carbohydrate wall material and modified starch, 0.01 to 10 parts of antioxidant, 0 to 5 parts of optional glidant, 0 to 5 parts of optional flavoring agent and 0 to 5 parts of optional coloring agent, the polyunsaturated fatty acid source comprises an ω-6 source and an ω-3 source, the ω-6 and the ω-3 in the polyunsaturated fatty acid source have a mass ratio of (0.5 to 4):1, and the antioxidant is a water-phase antioxidant and/or oil-phase antioxidant, and the method comprises:

(1) the water-phase wall material, part of vitamin E-polyethylene glycol succinate and optional water-phase antioxidant, glidant, flavoring agent and coloring agent are dispersed in water to obtain a water-phase material; the vitamin K2, polyunsaturated fatty acid source, the remaining vitamin E-polyethylene glycol succinate and optional oil-phase antioxidant are mixed uniformly to obtain an oil-phase material; the water-phase material and the oil-phase material have a vitamin E-polyethylene glycol succinate weight ratio of (2 to 6):1; and (2) the water-phase material and the oil-phase material are mixed, emulsified under high-speed shearing, and homogenized under a pressure of 30 to 50 MPa to obtain an emulsion with an oil droplet particle size of <100 nanometer, and then the obtained emulsion is subjected to spray-drying to obtain the vitamin K2 microcapsule.

2. The method for preparing vitamin K2 microcapsule according to claim 1, wherein the water-phase wall material in step (1), part of vitamin E-polyethylene glycol succinate and optional water-phase antioxidant, glidant, flavoring agent and coloring agent are dispersed in water by a method that comprises: dissolving the water-phase wall material in 35° C. to 45° C. water, performing ultrasonic dispersion under an inert atmosphere to obtain a wall material aqueous solution, passing the solution through an ultrasonic probe in a countercurrent circulation mode, and then adding the part of vitamin E-polyethylene glycol succinate and optional water-phase antioxidant, glidant, flavoring agent and coloring agent into the wall material aqueous solution, and mixing uniformly under an inert atmosphere to obtain the water-phase material.

3. The method for preparing vitamin K2 microcapsule according to claim 2, wherein the ultrasonic dispersion in step (1) is performed under a condition comprising an ultrasonic power of 240 to 480 W and an ultrasonic time of 10 to 30 min.

4. The method for preparing vitamin K2 microcapsule according to claim 1, wherein the vitamin K2, polyunsaturated fatty acid source, the remaining vitamin E-polyethylene glycol succinate and optional oil-phase antioxidant in step (1) are mixed uniformly by a method that comprises: heating the vitamin K2, polyunsaturated fatty acid source, the remaining vitamin E-polyethylene glycol succinate and optional oil-phase antioxidant under an inert atmosphere to 35° C. to 50° C., keeping warm and stirring until these components are completely dissolved, thereby obtaining the oil-phase material.

5. The method for preparing vitamin K2 microcapsule according to claim 1, wherein the water-phase material and the oil-phase material in step (2) are mixed by the method that further comprises: simultaneously discharging and mixing the water-phase material and the oil-phase material at a mass ratio of (1.5 to 2.5):1.

6. The method for preparing vitamin K2 microcapsule according to claim 1, wherein the spray-drying in step (2) is performed under a condition comprising a spray inlet air temperature of 140° C. to 170° C., an outlet air temperature of 80° C. of 95° C., an atomizer frequency of 165 to 200 Hz, a cooling air temperature of 16° C. to 22° C., and a feed temperature of 50° C. to 60° C.

7. The method for preparing vitamin K2 microcapsule according to claim 1, wherein the vitamin K2 microcapsule comprises the following components by weight: 0.005 to 5 parts of vitamin K2, 10 to 25 parts of polyunsaturated fatty acid source, 0.5 to 5 parts of vitamin E-polyethylene glycol succinate, 55 to 90 parts of water-phase wall material, 0.05 to 5 parts of antioxidant, 0 to 2 parts of glidant, 0 to 2 parts of flavoring agent and 0 to 2 parts of coloring agent.

8. The method for preparing vitamin K2 microcapsule according to claim 1, wherein the vitamin K2 is in the configuration of MK-7.

9. The method for preparing vitamin K2 microcapsule according to claim 1, wherein the ω-6 and the ω-3 in the polyunsaturated fatty acid source have a mass ratio of (1 to 2):1.

10. The method for preparing vitamin K2 microcapsule according to claim 9, wherein the ω-6 and the ω-3 in the polyunsaturated fatty acid source have a mass ratio of 1.5:1.

11. The method for preparing vitamin K2 microcapsule according to claim 1, wherein the ω-3 source is at least one selected from the group consisting of DHA algae oil, fish oil, linseed oil, *perilla* seed oil, low erucic acid rapeseed oil, walnut oil, zanthoxylum seed oil and soybean oil; and the ω-6 source is at least one selected from the group consisting of ARA oil, grape seed oil, safflower seed oil, soybean oil, low erucic acid rapeseed oil, walnut oil, sunflower seed oil and sesame oil.

12. The method for preparing vitamin K2 microcapsule according to claim 1, wherein the protein compound wall material is at least one selected from the group consisting of sodium caseinate, soy protein, gliadin and whey protein; the carbohydrate wall material is at least one selected from the group consisting of Arabic gum, white granulated sugar, cyclodextrin, maltodextrin, solid corn syrup and dry glucose syrup; and the modified starch is starch sodium octenyl succinate and/or starch sodium dodecenyl succinate.

13. The method for preparing vitamin K2 microcapsule according to claim 1, wherein the water-phase antioxidant is at least one selected from the group consisting of sodium ascorbate, ascorbic acid and sodium citrate; and the oil-phase antioxidant is at least one selected from the group consisting of lecithin, natural VE, rosemary extract, and ascorbyl palmitate.

14. A vitamin K2 microcapsule, which is prepared by the method according to claim 1.

15. A method for preventing or treating cardiovascular and cerebrovascular diseases, comprising administering to a subject in need an effective amount of the vitamin K2 microcapsule according to claim 14.

* * * * *